(12) United States Patent
Schlienger et al.

(10) Patent No.: US 8,518,040 B2
(45) Date of Patent: Aug. 27, 2013

(54) INTRAMEDULLARY NAIL

(75) Inventors: Andre Schlienger, Basel (CH); Markus Buettler, Oensingen (CH); Peter Senn, Waldenburg (CH)

(73) Assignee: Depuy Synthes Products, LLC, Raynham, MA (US)

( * ) Notice: Subject to any disclaimer, the term of this patent is extended or adjusted under 35 U.S.C. 154(b) by 185 days.

(21) Appl. No.: 13/005,161

(22) Filed: Jan. 12, 2011

(65) Prior Publication Data

US 2011/0106080 A1   May 5, 2011

Related U.S. Application Data

(63) Continuation of application No. 11/570,674, filed as application No. PCT/CH2004/000379 on Jun. 22, 2004, now Pat. No. 7,892,234.

(51) Int. Cl.
*A61B 17/56* (2006.01)
*A61B 17/58* (2006.01)
*A61F 2/30* (2006.01)

(52) U.S. Cl.
USPC .............................................. 606/62; 606/64

(58) Field of Classification Search
USPC ........ 606/59, 62–68, 95–98, 329; 623/23.23, 623/23.33, 47–56; 411/439, 441, 442
See application file for complete search history.

(56) References Cited

U.S. PATENT DOCUMENTS 5,549,610 A * 8/1996 Russell et al. .................. 606/64

* cited by examiner

*Primary Examiner* — Eduardo C Robert
*Assistant Examiner* — Christina Negrellirodriguez
(74) *Attorney, Agent, or Firm* — Fay Kaplun & Marcin, LLP

(57) ABSTRACT

An intramedullary nail includes (a) a longitudinal nail body extending from a proximal end to a distal end and having a central longitudinal axis and a diameter D, the nail body being configured for insertion into a medullary cavity of a bone, the nail body having a proximal portion and a distal portion longitudinally separated from one another; (b) a first transverse hole extending through the distal portion of the nail body at an angle transverse to the central longitudinal axis and defining a first transverse hole axis, the first transverse hole axis being offset from the central longitudinal axis of the nail body; and (c) a second transverse hole extending through the distal portion of the nail body at an angle transverse to the central longitudinal axis and defining a second transverse hole axis. The first transverse hole axis intersects the second transverse hole axis.

15 Claims, 2 Drawing Sheets

INTRAMEDULLARY NAIL

RELATED APPLICATION DATA

This application is a Continuation Application of U.S. patent application Ser. No. 11/570,674 filed on Jul. 20, 2007, which is the U.S. National Stage application of PCT Application Ser. No. PCT/CH2004/000379 filed on Jun. 22, 2004, the entire content of these applications are expressly incorporated herein by reference thereto.

FIELD OF THE INVENTION

The present invention concerns an intramedullary nail for use in repairing bone fractures and, more particularly, an intramedullary nail for use in repairing fractures of the distal tibia.

BACKGROUND OF THE INVENTION

An intramedullary nail of this kind is known from EP Patent No. 1 024 762 to LEU. This known intramedullary nail comprises several transversal distal holes, whose borehole axes all cross the intramedullary nail's central line. The disadvantage of this transversal hole setup is that the introduction of the force for the forces to be transmitted through the intramedullary nail occurs in a bone volume whose dimensions transversal to the central axis are limited to the diameter of the locking screws and are therefore stressing the same bone fibres in a longitudinal direction.

SUMMARY OF THE INVENTION

The present invention relates to an intramedullary nail which allows a high degree of locking stability and introduction of force, for the forces to be transmitted across the intramedullary nail that is optimally distributed over the cross section of the bone.

In particular, the present invention relates to an intramedullary nail which includes a longitudinal nail body having a total length, a distal stem portion and a proximal portion, the distal stem portion having an outer diameter D and configured and dimensioned for insertion into a medullary canal of a bone. The longitudinal nail body defines a central longitudinal axis coaxial with a line connecting a first center of gravity of a first transverse cross-section taken through the nail body orthogonal to the central longitudinal axis with a second center of gravity of a second transverse cross-section taken through the nail body orthogonal to the central longitudinal axis. At least a first through-hole and a second through-hole are formed in the distal stem portion transverse to the central longitudinal axis, the first through-hole having a radius $R_1$ and defining a first central hole axis transverse to the central longitudinal axis and the second through-hole having a radius $R_2$ and defining a second central hole axis transverse to the central longitudinal axis. At least one of the first and second central holes axes is offset a distance $d_1>0$ from the central longitudinal axis of the nail body, and $(d_1+R_1)<(D/2)$, such that the mantle surfaces of each of the two through-holes are wholly inside the intramedullary nail body.

Some of the advantages of the present invention are as follows:

The locking stability is boosted by the additional asymmetry of the distal locking mechanism;

The introduction of the forces to be transmitted across the intramedullary nail is optimally distributed over the cross section of the bone; and The same bone fibres are not stressed in a longitudinal direction.

In a special form of embodiment the borehole axes of at least two cross holes exhibit distances $d_1>0$ and $d_2>0$ with respect to the central line.

In another form of embodiment, the borehole axes of the at least two cross holes run past the central line on opposite sides. The advantage of this embodiment is based on the fact that the bone screws capable of being introduced in both cross holes are not stressing the same bone fibre of the tubular bone.

In a further form of embodiment, the borehole axis of the at least one cross hole is set in a plane orthogonal to the central line at a distance $d_1$.

In an additional form of embodiment, the distances $d_1$ and $d_2$ are, with respect to the diameter D, in a range of $0.0001 D<d<0.6000 D$, and preferably in a range of $0.2D<d<0.5 D$, respectively.

In another form of embodiment the intramedullary nail includes a channel coaxial to the central line.

The orthogonal cross-sectional surfaces of the intramedullary nail can preferably be conformed in a circular or circle-shaped form.

In a special form of embodiment the at least two cross holes are placed in the distal half of the intramedullary nail.

The distance d is advantageously larger than 0.5 mm and preferably larger than 1.0 mm. However, the distance $d_1$ is properly smaller than 0.5 mm and preferably smaller than 3.5 mm. The distance $d_1$ depends up to a certain point on the diameter of the intramedullary nail. The $D/d_1$ ratio between the diameter D of the intramedullary nail and the distance $d_1$ should therefore properly be larger than 5, preferably larger than 8. On the other hand, the $D/d_1$ ratio between the diameter D of the intramedullary nail and the distance $d_1$ should properly be smaller than 25, preferably smaller than 21.

In another form of embodiment, the mantle surfaces of the at least two cross holes are fully embedded inside the intramedullary nail, meaning that the cross holes open only when entering and leaving the intramedullary nail, and are for the rest wholly extended inside the intramedullary nail.

BRIEF DESCRIPTION OF THE DRAWINGS

The present invention and developments of the invention will be clarified in further detail below, by using schematic representations of several examples of preferred embodiments.

DETAILED DESCRIPTION

Figure 1:
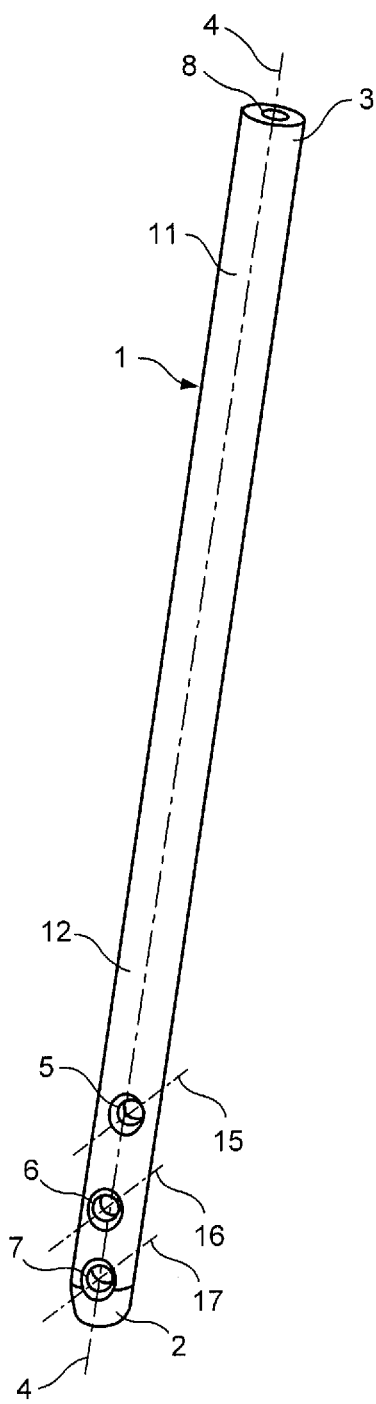
FIG. 1 is a perspective view of an intramedullary nail according to an exemplary embodiment of the present invention.
Figure 2:
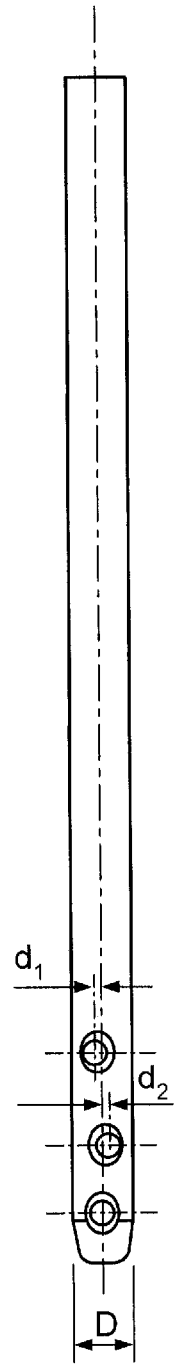
FIG. 2 is a side view of the intramedullary nail according to FIG. 1.
Figure 3:
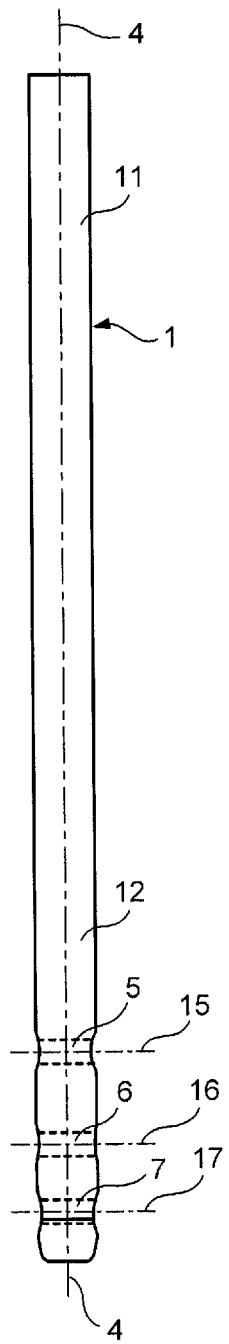
FIG. 3 is a side view of the intramedullary nail according to an exemplary embodiment of the present invention, turned 90° with respect to FIG. 2.

The form of embodiment of an intramedullary nail shown in FIG. 1-3 has a proximal half 11, a distal half 12 suitable for introducing it into the medullary channel, and a central line 4. The intramedullary nail 1 exhibits an essentially constant diameter D and is penetrated by a channel 8 from its proximal end 3 to its distal end 2. The distal half presents three cross holes capable of receiving locking screws 5, 6, 7 (not shown). The most proximally situated cross hole 5 has a borehole axis 15, the middle cross hole 6 has a borehole axis 16 and the most distal cross hole 7 a borehole axis 17. The cross holes 5, 6, 7 are arranged so that their borehole axes 15; 16; 17 are parallel to each other. The diameter of the intramedullary nail 1 amounts to D=10 mm. The borehole axis 15 of the cross hole 5 has a distance $d_1$=0.5 mm with respect to the central line 4. The borehole axis 16 of the cross hole 6 also has a distance $d_2$=0.5 mm with respect to the central axis 4, but on the opposite side. Only the cross hole set in the most distal position 7 has a borehole axis 17 that intersects the central line 4. The most proximal and the middle cross holes 5, 6 are offset with respect to the perimeter of the intramedullary nail 1 only to the degree of not piercing the outer mantle surface of the intramedullary nail 1.

Figure 4:
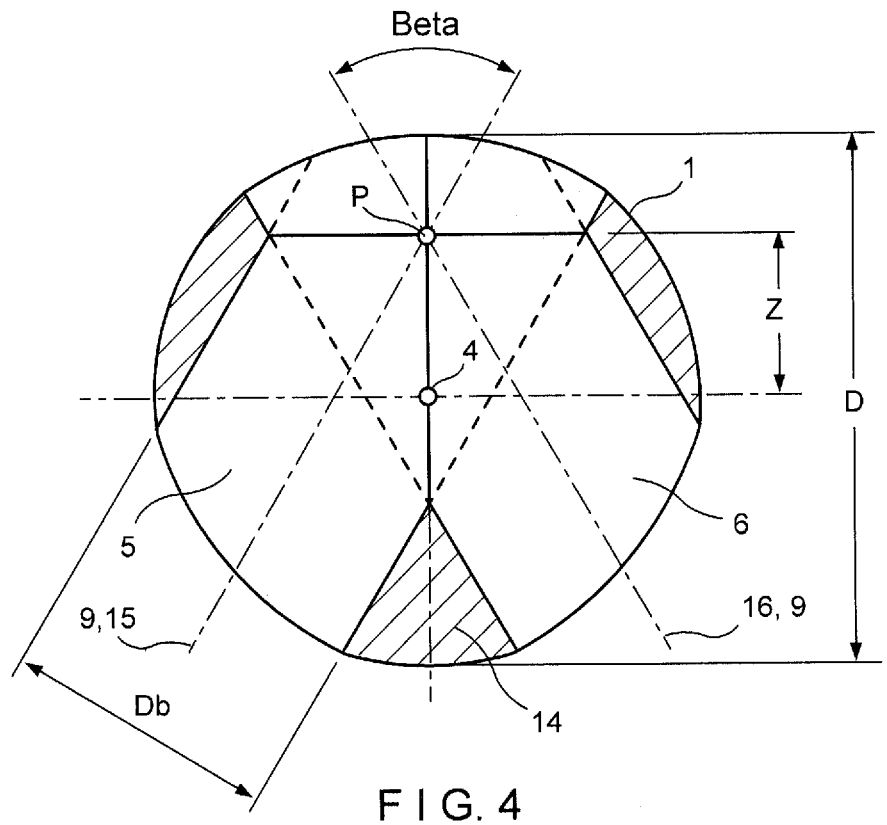
FIG. 4 is an orthogonal cross section view across an intramedullary nail modified with respect to the medullary nail according to FIGS. 1-3.
Figure 5:
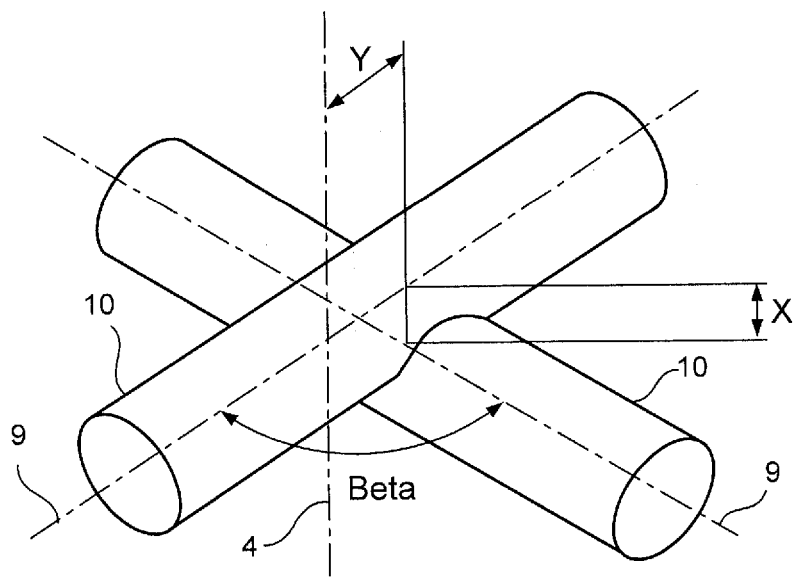
FIG. 5 is a perspective view of the virtual borehole cylinder of another form of embodiment of the intramedullary nail.

FIG. 4 shows a further form of embodiment of the intramedullary nail 1, which differs from the form of embodiment shown in FIG. 1-3 in that the virtual borehole cylinders 10 of two adjacent cross holes 5, 6—just like in the form of embodiment according to FIG. 5—penetrate each other. The cylinder axes 9 of both virtual borehole cylinders 10 correspond to the borehole axes 15; 16 of the two cross holes 5; 6 and intersect each other in point P, which has a distance z=0.4 D from the central line 4. In other words, the point P does not fall on the central line 4 of the intramedullary nail. The virtual borehole cylinders 10 have two separate inlets in the intramedullary nail 1, but only one common outlet from the intramedullary nail. The cylinder axes 9 of the two virtual borehole cylinders 10 fall into a plane orthogonal to the central line 4, which corresponds to the drawing plane of FIG. 4. The cylinder axes 9 of the two virtual borehole cylinders 10 can however also lie in a plane which is penetrated by the longitudinal axis 4 under an angle deviating from 90°.

In the example shown, the cylinder axes 9 of the two virtual borehole cylinder 10 cross each other under an angle β of 60°. In the example shown, the diameter $D_b$ of the virtual borehole cylinder 10 in the example is equal to 0.3 times D.

FIG. 5 shows another form of embodiment of the intramedullary nail 1, wherein the cylinder axes 9 of the two virtual borehole cylinders 10 can also run at an oblique angle and have the shortest distance x to each other which is smaller than half the sum of the two diameters $D_b$ of the virtual borehole cylinder 10. In the example shown here, the shortest distance x between the two oblique cylinder axes 9 runs parallel to the longitudinal axis 4 and has a shortest distance y>0 to the same. However, the length defined by the shortest distance x can also run obliquely to the longitudinal axis 4. The distance y is in the range of D/2>y>0.4 D. The cylinder axes 9 of the two virtual borehole cylinders 10 separate at this point under an angle β of 90°.

The invention claimed is:

1. An intramedullary nail, comprising:
    a longitudinal nail body extending from a proximal end to a distal end and having a central longitudinal axis and a diameter D, the nail body being configured for insertion into a medullary cavity of a bone, the nail body having a proximal portion and a distal portion longitudinally separated from one another;
    a first transverse hole extending through the distal portion of the nail body at an angle transverse to the central longitudinal axis and defining a first transverse hole axis, the first transverse hole axis being offset from the central longitudinal axis of the nail body by a distance $d_1$>0 such that the first transverse hole axis does not intersect the central longitudinal axis; and
    a second transverse hole extending through the distal portion of the nail body at an angle transverse to the central longitudinal axis and defining a second transverse hole axis;
    wherein the first transverse hole axis intersects the second transverse hole axis.

2. The intramedullary nail of claim 1, wherein the first transverse hole axis intersects the second transverse hole axis at a point P separated from the central longitudinal axis.

3. The intramedullary nail of claim 2, wherein the point P is separated from the central longitudinal axis by a distance z, where z is equal to approximately 0.4D.

4. The intramedullary nail of claim 2, wherein the point P is separated from the central longitudinal axis by a distance y in the range of D/2<y<0.4D.

5. The intramedullary nail of claim 1, wherein the first transverse hole has a first inlet and a first outlet and the second transverse hole has a second inlet and a second outlet.

6. The intramedullary nail of claim 1, wherein the first transverse hole has a first inlet and the second transverse hole has a second inlet and wherein the first and second transverse holes have a common outlet.

7. The intramedullary nail of claim 1, wherein the first and second transverse holes axes lie in a plane penetrating the central longitudinal axis at an angle smaller than 90°.

8. The intramedullary nail of claim 1, wherein the first and second transverse holes axes lie in a plane penetrating the central longitudinal axis at an angle of approximately 90°.

9. The intramedullary nail of claim 1, wherein a diameter $D_1$ of the first transverse hole is equal to 0.3D.

10. The intramedullary nail of claim 1, wherein the first transverse hole axis is longitudinally offset from the second transverse hole axis along the central longitudinal axis by a distance x.

11. The intramedullary nail of claim 10, wherein x<($D_1$+$D_2$)/2, wherein $D_1$ is a diameter of the first transverse hole and $D_2$ is a diameter of the second transverse hole.

12. The intramedullary nail of claim 10, wherein the distance x extend parallel to the central longitudinal axis.

13. The intramedullary nail of claim 10, wherein the distance x extends obliquely to the central longitudinal axis.

14. A bone fixation method, comprising:
    inserting an intramedullary nail into a medullary canal of a bone, the intramedullary nail including a longitudinal nail body extending from a proximal end to a distal end and having a central longitudinal axis, the intramedullary nail having a diameter D, the nail body having a proximal portion and a distal portion longitudinally separated from one another, a first transverse hole extending through the distal portion of the nail body at an angle transverse to the central longitudinal axis and defining a first transverse hole axis, the first transverse hole axis being offset from the central longitudinal axis of the nail body by a distance $d_1$>0 such that the first transverse hole axis does not intersect the central longitudinal axis, and a second transverse hole extending through the distal portion of the nail body at an angle transverse to the central longitudinal axis and defining a second transverse hole axis, wherein the first transverse hole axis intersects the second transverse hole axis; and
    inserting a bone fastener into one of the first and second transverse holes.

15. The method of claim 14, wherein the first transverse hole axis intersects the second transverse hole axis at a point P separated from the central longitudinal axis by a distance z, where z is equal to approximately 0.4D.

* * * * *